(12) United States Patent
Mathew et al.

(10) Patent No.: US 7,717,849 B2
(45) Date of Patent: May 18, 2010

(54) METHOD AND APPARATUS FOR CONTROLLING ULTRASOUND SYSTEM DISPLAY

(75) Inventors: Prakash Parayil Mathew, Mukwonago, WI (US); Michelle Ganiere Angle, Muskego, WI (US); Steven Charles Miller, Waukesha, WI (US)

(73) Assignee: Gerneral Electric Company, Schenectady, NY (US)

( * ) Notice: Subject to any disclaimer, the term of this patent is extended or adjusted under 35 U.S.C. 154(b) by 1319 days.

(21) Appl. No.: 10/885,352

(22) Filed: Jul. 6, 2004

(65) Prior Publication Data

US 2006/0020202 A1 Jan. 26, 2006

(51) Int. Cl.
*A61B 8/00* (2006.01)

(52) U.S. Cl. ................................ 600/437; 382/128

(58) Field of Classification Search ............. 600/437, 600/407, 410, 425; 382/128; 345/419
See application file for complete search history.

(56) References Cited

U.S. PATENT DOCUMENTS

| | | | | |
|---|---|---|---|---|
| 4,790,321 A * | 12/1988 | Miwa et al. | ............. | 600/443 |
| 5,079,699 A | 1/1992 | Tuy et al. | | |
| 5,159,931 A | 11/1992 | Pini | | |
| 5,274,551 A * | 12/1993 | Corby, Jr. | ............. | 600/433 |
| 5,297,043 A | 3/1994 | Tuy et al. | | |
| 5,421,332 A * | 6/1995 | Ishii et al. | ............. | 600/443 |
| 5,488,952 A * | 2/1996 | Schoolman | ............. | 600/443 |
| 5,515,849 A * | 5/1996 | Murashita et al. | ............. | 600/479 |
| 5,724,976 A | 3/1998 | Mine et al. | | |
| 5,806,521 A | 9/1998 | Morimoto et al. | | |
| 6,242,916 B1 | 6/2001 | King | | |
| 6,243,488 B1 | 6/2001 | Penna | | |
| 6,368,330 B1 * | 4/2002 | Hynes et al. | ............. | 606/130 |
| 6,369,812 B1 * | 4/2002 | Iyriboz et al. | ............. | 345/419 |
| 6,487,432 B2 | 11/2002 | Slack | | |
| 6,571,227 B1 | 5/2003 | Agrafiotis et al. | | |
| 6,590,573 B1 | 7/2003 | Geshwind | | |
| 6,597,818 B2 | 7/2003 | Kumar et al. | | |
| 6,618,609 B2 | 9/2003 | Liu et al. | | |
| 7,212,661 B2 * | 5/2007 | Samara et al. | ............. | 382/131 |
| 2002/0064382 A1 | 5/2002 | Hildreth et al. | | |
| 2002/0113787 A1 * | 8/2002 | Ray et al. | ............. | 345/424 |
| 2003/0073910 A1 | 4/2003 | Chance | | |
| 2004/0073111 A1 * | 4/2004 | Poland et al. | ............. | 600/437 |
| 2004/0086175 A1 * | 5/2004 | Parker et al. | ............. | 382/154 |
| 2004/0249291 A1 * | 12/2004 | Honda et al. | ............. | 600/476 |
| 2004/0254439 A1 * | 12/2004 | Fowkes et al. | ............. | 600/407 |
| 2005/0111761 A1 * | 5/2005 | Mathew et al. | ............. | 382/305 |
| 2005/0283075 A1 * | 12/2005 | Ma et al. | ............. | 600/441 |

OTHER PUBLICATIONS

Bushberg, J.T. et al, The Essential Physics of Medical Imaging, 2002, Lippincott, Williams, and Wilkins, p. 522.*

* cited by examiner

*Primary Examiner*—Brian Casler
*Assistant Examiner*—Jonathan G Cwern
(74) *Attorney, Agent, or Firm*—Dean Small; Small Patent Law Group

(57) ABSTRACT

A method for operating a medical imaging system is provided. The method includes receiving an image data set of a region of interest in a first dimensional representation, reducing the dimensionality of the image data set to a second dimensional representation, selecting a feature of interest in the second dimensional representation, and generating an image of the selected feature in the first dimensional representation.

36 Claims, 3 Drawing Sheets

METHOD AND APPARATUS FOR CONTROLLING ULTRASOUND SYSTEM DISPLAY

BACKGROUND OF THE INVENTION

This invention relates generally to ultrasound systems and, more particularly, to methods and devices for controlling imaging in ultrasound systems.

At least some known ultrasound systems, for example, an ultrasound machine or scanner, are capable of performing three dimensional (3D) volume date acquisition and acquisition of the 3D data sets progressing over time (4D). Raw data and processed data of the 3D and 4D data sets may grow exponentially as multiple dimensional data are spanned. Large data sets can make managing and manipulating the data hardware intensive, such as requiring large amounts of random access memory (RAM), large disk storage, powerful microprocessors, and image handling chipsets. The large data sets also may make navigating though the data, locating an object of interest, and displaying a desired view of the object of interest cumbersome and difficult. Because the physical space on the ultrasound machine may be limited, it is often not possible to provide a real-time or offline 3D or 4D representation of the data available to the user at all times.

A common approach to managing the limited space for data and display capabilities is to use only a portion of the data, such as every Nth frame or image of a plurality of images that make up a data set. However, using only every Nth frame or image may result in the omission of data for which a user is searching. Additionally, allowing a user to view only a portion of the data may not represent the data in a manner familiar to the user.

BRIEF DESCRIPTION OF THE INVENTION

In one embodiment, a method for operating a medical imaging system is provided. The method includes receiving an image data set of a region of interest in a first dimensional representation, reducing the dimensionality of the image data set to a second dimensional representation, selecting a feature of interest in the second dimensional representation, and generating an image corresponding to the selected feature in the first dimensional representation.

In another embodiment, an ultrasound system is provided. The ultrasound system includes an ultrasound probe having at least one transducer for transmitting pulses to an object, a processor programmed to receive image data in a first dimensionality and convert the image data to a second dimensionality, a viewpoint selector coupled to a user input of said ultrasound system to control a view of converted image data, and a display system configured to display an ultrasound image portion and a reduced dimensionality image portion.

In another embodiment, a method for processing ultrasound data is provided. The method includes receiving multidimensional ultrasound data representing an image, generating a reduced dimension data set from the multidimensional ultrasound data, selecting a feature of interest in the reduced dimension data set, and displaying the image corresponding to the feature of interest.

DETAILED DESCRIPTION OF THE INVENTION

Exemplary embodiments of ultrasound systems and methods for controlling such systems are described in detail below. A detailed description of exemplary ultrasound systems will first be provided followed by a detailed description of an embodiment that facilitates managing, navigating, and displaying image data in ultrasound systems.

Figure 1:
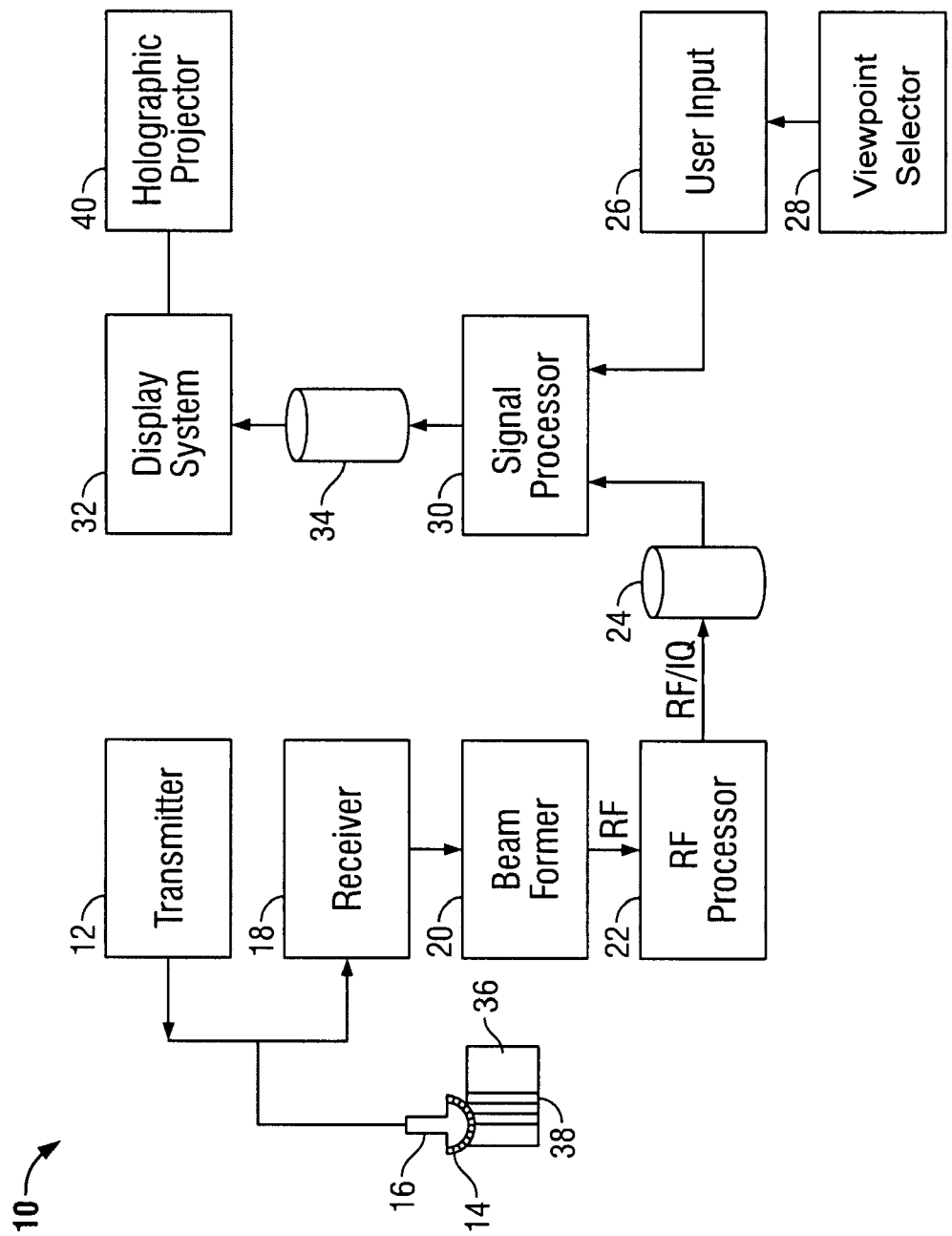
FIG. 1 is a block diagram of an ultrasound system in accordance with one exemplary embodiment of the present invention.

FIG. 1 is a block diagram of an ultrasound system in accordance with one exemplary embodiment of the present invention. Ultrasound system 10 includes a transmitter 12 that drives transducer elements 14 within a probe 16 to emit pulsed ultrasonic signals into a body. A variety of geometries may be used. The ultrasonic signals are back-scattered from structures in the body, like blood cells or muscular tissue, to produce echoes that return to transducer elements 14. The echoes are received by a receiver 18. The received echoes are provided to a beamformer 20, which performs beamforming and outputs an RF signal. The RF signal is then transmitted to an RF processor 22. Alternatively, RF processor 22 may include a complex demodulator (not shown) that demodulates the RF signal to form IQ data pairs representative of the echo signals. The RF or IQ signal data may then be routed directly to an RF/IQ buffer 24 for temporary storage. A user input device 26 as described herein may be used to control operation of ultrasound system 10. This may include using voice commands to control a viewpoint selector 28, which allows a user to select a virtual vantage point from which to view the image data, or view perspective, a region of interest, and/or an index indicator for controlling ultrasound system 10.

Ultrasound system 10 also includes a processor 30 to process the acquired ultrasound information (i.e., RF signal data or IQ data pairs) and prepare frames of ultrasound information for display on display system 32. Processor 30 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 24 during a scanning session and processed in less than real-time in a live or off-line operation.

Ultrasound system 10 may continuously acquire ultrasound information at a frame rate that exceeds fifty frames per second, which is the approximate perception rate of the human eye. The acquired ultrasound information may be displayed on display system 32 at a slower frame-rate. An image buffer 34 may be included for storing processed frames of acquired ultrasound information that are not scheduled to be displayed immediately. In an exemplary embodiment, image buffer 34 is of sufficient capacity to store at least several seconds of frames of ultrasound information. The frames of ultrasound information are stored in a manner to facilitate retrieval thereof according to its order or time of acquisition. Image buffer 34 may comprise any known data storage medium.

It should be noted that various embodiments of a user interface or input, such as, for example, user input device 26, may be implemented for controlling ultrasound system 10. Such various embodiments may include control functionality, such as a set of user controls for controlling ultrasound system 10. The set of user controls may be provided, for example, as part of a touch screen or panel, or as manual inputs, including, for example, user operable switches, and/or buttons. The set of user controls may be manually operable or voice operated.

Ultrasound system 10 includes a probe 16, such as, for example, a transducer or a plurality of transducing elements, connected to a transmitter 12 and a receiver 18. Probe 16 transmits ultrasonic pulses and receives echoes from structures inside a scanned volume 36. Scanned volume 36 may be obtained by various techniques, including, for example, real-time imaging, volume scanning, scanning with transducers having positioning sensors, freehand scanning using a Voxel correlation technique or scanning with matrix array transducers.

Probe 16 may be moved, such as, along a linear or arcuate path, while scanning volume 36. At each linear or arcuate position, probe 16 obtains one or more scan planes 38. Scan planes 38 are collected for a thickness, such as from a group or set of adjacent scan planes 38. Scan planes 38 may be stored in buffer 24, and then transmitted to processor 30. In some embodiments, probe 16 may obtain lines instead of scan planes 38, and buffer 24 may store lines obtained by probe 16 rather than scan planes 38. Buffer 24 then stores lines obtained by probe 16 rather than scan planes 38. Processor 30 may receive a slice thickness setting from a slice thickness setting control within user input 26 or may set the slice thickness setting control automatically based on predetermined characteristics of the transmitted data, which identifies the thickness of a slice to be created from scan planes 38. Processor 30 creates a data slice from multiple adjacent scan planes 38. The number of adjacent scan planes 38 that may be obtained to form each data slice is dependent upon the thickness selected by the slice thickness setting control. The data slice is stored in image buffer 34 and processor 30 may access image buffer 34 to perform volume rendering upon the data slice.

Processor 30 may also generate difference maps of the stored data or may create difference maps of incoming data in real-time. For example, a difference map of respective pixels of each adjacent pair of planar slices may be generated using an intensity projection map, a sum of absolute differences, a maximum intensity projection map, a minimum intensity projection map, an average intensity projection map, an integrated projection map, a first local maximum projection map, and an arbitrarily weighted projection map. The output of the difference maps may be indexed and combined to reduce the dimensionality of the incoming data. For example, difference maps of adjacent pairs of image slices may be combined to render a two-dimensional indication of differences between all of the plurality of image slices. The indication may indicate relative values of the difference between adjacent planar slices on a display that may be traversed to quickly locate a feature of interest, such as, a portion of the display where there are relatively larger differences between adjacent planar slices than other portions. Similarly, volume data collected over time may be reduced in dimensionality by generating difference maps of temporally adjacent volumes such that a region of interest may be selected or a portion of the display that represents a greater relative change in difference over time may be selected.

The output of processor 30 may be selectably transmitted to a display system 32. Display system 32 may comprise a user wearable device such as a texture glove, a headset display, and/or a heads-up display. As used herein, a texture glove is a wearable covering for a limb comprising a plurality of sensors for transmitting the limb's movement and orientation in space to an input device or directly to a processor. The texture glove may include a plurality of sensory outputs that interact with the limb to transmit sensory indications of, for example, but not limited to, texture, temperature, force, pressure, and orientation. Display system 32 may include an active-matrix color LCD display, such as is available from Sharp Systems of America, Mahwah, N.J., wherein a second matrix, or parallax barrier is transparent when operating in a 2-D mode. During a user selectable 3-D mode a switching LCD sends alternate pixels to the left and right eyes of the user to create a 3-D effect.

Display system 32 may also include or may transmit images to a holographic projection device 40, which may display images in a heads-up mode such that projected images are used in conjunction with a users visual field to highlight or accentuate features in the user's visual field, or may be used to comprise the entire visual display. Accordingly, holographic projection device 40 may be a head-mountable wearable device that includes sensors to determine a position and orientation of holographic projection device 40 relative to an object that is being scanned and/or has been scanned.

It should be noted that the position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

It should further be noted that ultrasound system 10 may include additional or different components. For example, a user interface or input may be provided and used to control the operation of ultrasound system 10, including, to control the input of patient data, scan parameters, and/or a change of scan mode.

Figure 2:
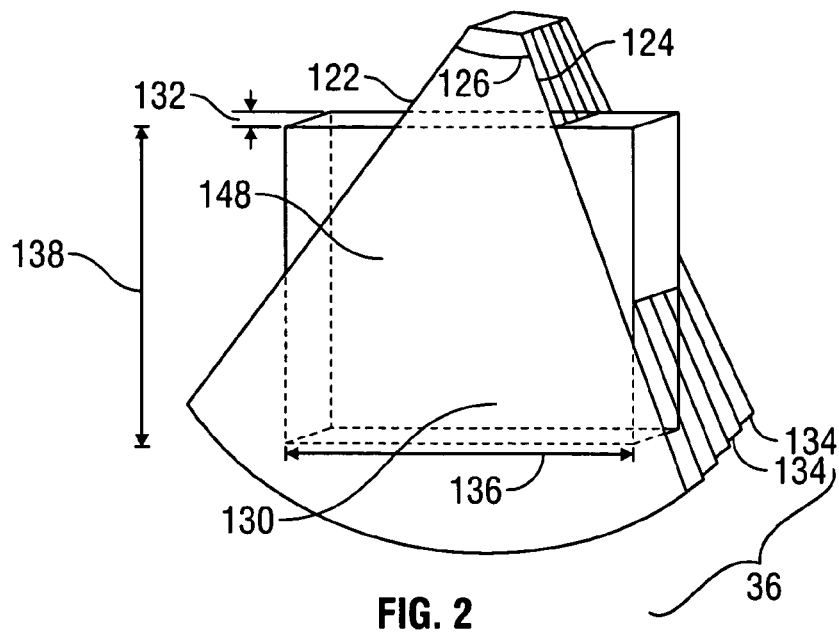
FIG. 2 is a perspective view of a real-time volume acquired by the system of FIG. 1 in accordance with an exemplary embodiment of the present invention.

FIG. 2 is a perspective view of a real-time volume acquired by the system of FIG. 1 in accordance with an exemplary embodiment of the present invention. Scanned volume 36 includes a sector shaped cross-section with radial borders 122 and 124 diverging from one another at an angle 126. Probe 16 (shown in FIG. 1) electronically focuses and directs ultrasound firings longitudinally to scan along adjacent scan lines in each scan plane 38 (shown in FIG. 1) and electronically or mechanically focuses and directs ultrasound firings laterally to scan adjacent scan planes 38. Scan planes 38 obtained by probe 16 may be stored in buffer 24 and may be scan converted from spherical to Cartesian coordinates by processor 30. A volume comprising multiple image planes 134 defined by multiple scan planes is generated as a rendering box 130. Rendering box 130 is formed from multiple adjacent image planes 134.

Rendering box 130 may be defined in size by an operator using user interface or input 26 to have a slice thickness 132, width 136 and height 138. Processor 30 may be controlled by the slice thickness setting control to adjust the thickness parameter of the slice to form rendering box 130 with the desired thickness. Rendering box 130 designates the portion of scanned volume 36 that is volume rendered. Processor 30 may access image buffer 34 renders along slice thickness 132 of rendering box 130.

Referring now to FIGS. 1 and 2, during operation, a slice having a pre-defined thickness is acquired and is processed in processor 30. The echo data representing rendering box 130 may be stored in image buffer. A predefined thickness of between about two millimeters and about twenty millimeters is typical, however, a thickness of less than about two millimeters or greater than about twenty millimeters also may be suitable depending on the application and the size of the area to be scanned. The slice thickness setting control may include a rotatable knob with discrete or continuous thickness settings.

Processor 30 projects rendering box 130 onto an image portion 148 of an image plane 134. Following processing, the pixel data in image portion 148 may be transmitted through a video processor within display system 32. Rendering box 130 may be located at any position and oriented at any direction within scanned volume 36. In some situations, depending on the size of the region being scanned, it may be advantageous for the rendering box 130 to be only a small portion of scanned volume 36.

Figure 3:
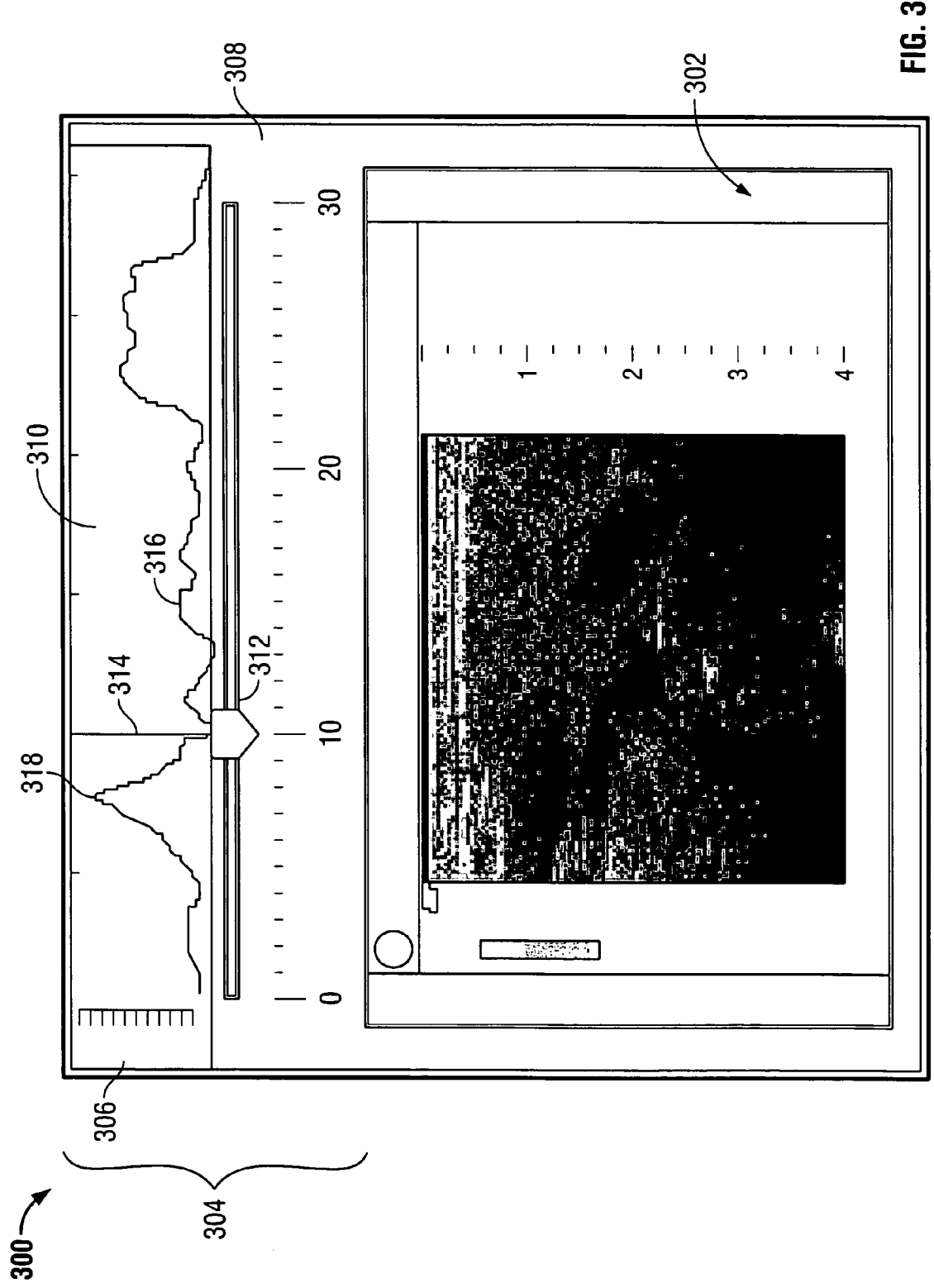
FIG. 3 is an exemplary embodiment of a user interface displaying an output of the ultrasound system shown in FIG. 1.

FIG. 3 is an exemplary embodiment of a user interface 300 displaying an output of ultrasound system 10 (shown in FIG. 1). User interface 300 may include an ultrasound viewing area 302 that may be used to display in real time 2D images, 2D images in less than real time, cine loops of 2D images, and 3D display of ultrasound images. Captured cine loops may be replayed in real time, at reduced speed or frame by frame in viewing area 302. Ultrasound viewing area 302 may be used to display difference maps of selected data to facilitate navigation of large amounts of image data to features of interest rapidly. User interface 300 may include a scout map area 304 that includes a scale 306 and an index indicator 308. A reduced dimensionality display 310 is used to indicate a relative difference between adjacent data slices and/or between temporally adjacent volumes. Scout map area 304 includes a selector 312 that may be used to move a cursor 314 relative to display 310. Cursor 314 indicates the portion of display 310 that is being displayed on ultrasound viewing area 302. In the exemplary embodiment, selector 312 is a slider. In other embodiments selector 312 may be, for example a toggle switch, or a numeric input field.

During a scan, an amount of data is received by system 10. Processor 30 computes a difference map of each pair of data slices contained with in the received data. The user may alter the view perspective of the image data displayed on ultrasound viewing area 302 to orient the view of each displayed image slice or difference map depending on a desired angle of view towards the scanned data. Ultrasound viewing area 302 may selectably display real time images and/or images that are stored on system 10. When system 10 computes difference maps for the adjacent image slices, a total difference between each pair of image slices may be computed and normalized for display on display 310. An exemplary trace 316 illustrates exemplary values for differences between adjacent image slices contained in the memory of system 10. A user may use slider 312 to move cursor 314 to a local maxima, such as feature of interest 318. A relatively large amount of difference between adjacent image slices may indicate a density interface between structures within scanned volume 36. Such a density interface may be between, for example, blood and a vessel wall, organ tissue and tumor tissue, and bone and muscle. After selecting a feature of interest 318, the user may select to replay the scan at full speed, reduced speed, frame-by-frame, or a combination of speeds. User interface 300 may similarly be used to find features of interest 318 in 3D data taken over time such that index indicator 308 represents an elapsed time of a scan. Accordingly, the user may select feature of interest and start playback of the image volume images in a selectable speed.

A view perspective may be selected from any direction relative to scanned volume 36. Accordingly, a difference map and reduced dimensionality display may be specified for a volume from any direction as selected by a user. The scanned volume may be navigated using a haptic input control, such as, but not limited to a mouse, a joystick, a jog wheel, and/or a texture glove coupled to user input 26. Selection of the view perspective direction may be performed using for example, a hardware button, a software key, and/or a virtual reality button or key.

Ultrasound viewing area 302 may be further used to increase a download rate of image data from system memory. Using a selected view perspective, system 10 may direct data from only a portion of memory to be downloaded. The downloaded data may correspond to only that amount of data containing data for the difference map selected, such that data that is not used for the difference map is not downloaded.

Processor 30 is also programmed to manipulate image data using software controls such as for example, spin, flip, and/or rotate on a 3D scout map, such that a quick multi-planar reformatting in arbitrary oblique planes simulates a "fly through" of the image displayed in non-linear trajectories. For example, this software also may be interfaced with a commercial visualization package, such as, Explorer™ Version 3.0, available from Numerical Applications Group, Downers Grove, Ill. The visualization package may be used to render and manipulate the image data. For example, these packages include viewers that allows a "fly through" of the difference maps and the 3D data set. The "fly-through" capability may be used to scout objects of interest, which may then be selected or otherwise identified for viewing using the full 3D data. Image data compression may be used that include lossy and/or lossless algorithms, such as, for example, IMCompress™, available from InnovMetrics Software, Quebec, Canada.

In the exemplary embodiments, system 10 may acquire 3D image data spanned over a period of time, or 4D data sets. Processor 30 may compute the differences between 3D data sets to measure a quantity of change between the 3D data sets. This change in quantity may be graphically displayed as a linear map such as display 310, to provide image representation information over a selected time span. For example, a greater value of change may signify a relatively more diagnostically interesting period in time, while a lower value of change may indicate that the diagnostic information within the period of time is relatively low. Processor 30 may automatically compute and display a difference map of received data over a period of time. The difference map may correspond to display 310 that illustrates an amount of image change between images over the period of time.

In the exemplary embodiment, a multi-dimensional structure, such as, a 3D structure, may be located within volume 36. A difference map of the multi-dimensional structure may be illustrated on ultrasound image area 302. Multi-dimensional structure may be identified manually via a user input while viewing the structure in a 3D rendering. The identified data may then be tagged such that processor 30 recognizes the tag associated with the data and provides an identification of the multi-dimensional structure on ultrasound image area 302. In an alternative embodiment, the multi-dimensional structure may be identified by matching features of the multi-dimensional structure with a plurality of structure models that may be stored in the memory of system 10. A comparison of model features to features of the multi-dimensional structure may be performed by processor 30 using, for example 3D image data, or may be performed using difference map data. Selection of a specific model to use for comparison and the comparison to the multi-dimensional structure may be performed automatically by processor 30. A user may reject the automatic selection using user input 26 wherein processor 30 may re-perform the selection and comparison process. Processor 30 may be programmed to "learn" from incorrect selections such that over time the selection of which model to use for comparing increases in accuracy.

Figure 4:
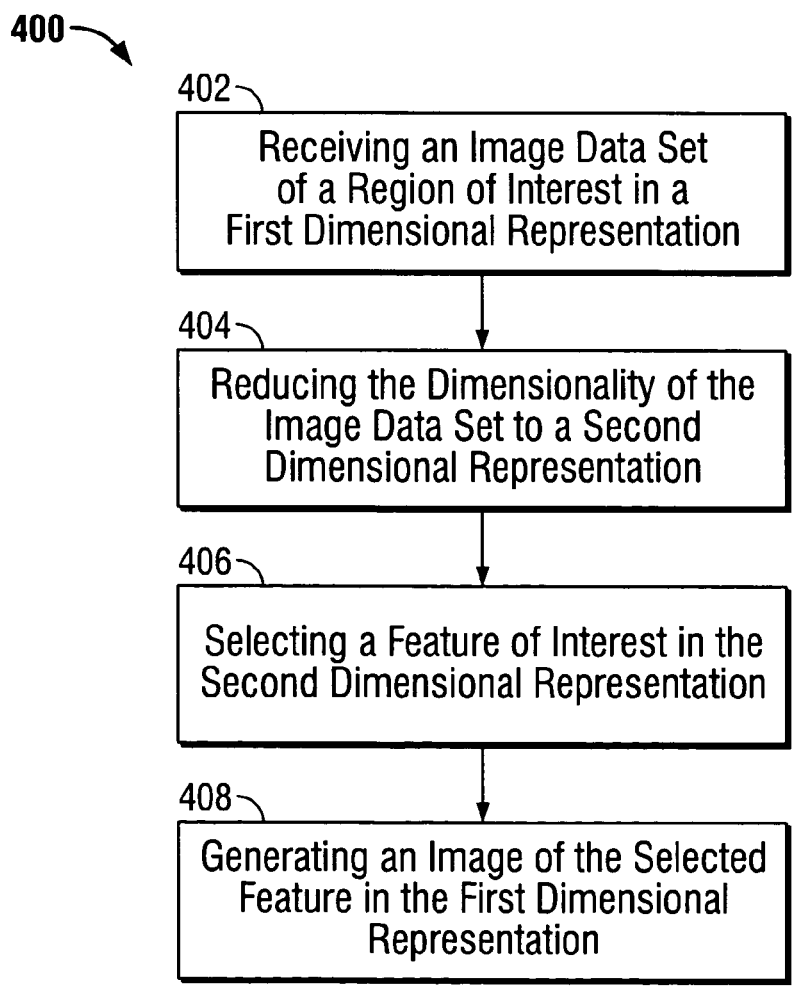
FIG. 4 is a flow chart of an exemplary method of displaying images for the ultrasound system shown in FIG. 1.

FIG. 4 is a flow chart of an exemplary method 400 of displaying images for ultrasound system 10 (shown in FIG. 1). Method 400 includes receiving 402 an image data set of a region of interest in a first dimensional representation, for example a 3D representation, and reducing 404 the dimensionality of the image data set to a second dimensional representation. For example, data received in a 3D representation may be difficult and time consuming to navigate, but reducing the dimensionality of the image data set also facilitates reducing the data representation of the image data, such that a feature of interest may be found in the reduced dimensionality image set and selected 406 for display by generating 408 an image of the selected feature in the first dimensional representation.

System 10 includes software and/or hardware controls for selecting views of images from a plurality of view perspectives using input devices associated with a view being displayed. A rendered volume may be rotated and/or flipped about a selectable axis to provide a view perspective from any direction. The rendered volume may then be sliced relative to the view perspective selected and reduced in dimensionality according to a selected difference map algorithm. The reduced dimensionality image display and the first dimensionality image display and/or a difference map display may be displayed on user interface 300. The reduced dimensionality display permits a user to quickly identify features of interest and locate the feature of interest. The feature of interest may be selected using a cursor and index indicator, and system 10 may then display the first dimensional representation of the feature of interest on ultrasound image area 302.

Image controls may be selectably included in user interface depending on whether the control function is available during a particular imaging procedure. For example, an image contrast control slider may only be displayed during a period when adjusting an image contrast is a permitted adjustment. Adjustment may be selectively permitted based on a setup for a particular user and/or a default set-up. Additionally, image controls may be selectively displayed and/or enabled based on a previous use history for each user or for all users. Image control input devices may comprise, but are not limited to, sliders, click selectors, and drop-down menus.

System 10 is also configured to receive input from a plurality of hardware pointing devices, such as, but not limited to, haptic controls for facilitating navigation through image representations. In the exemplary embodiment, processor 30 cooperates with the video processor within display system 32, and holographic projection device 40 to generate a holographic projection image of the image representation. Display system 32 and holographic projection device 40 may be configured to display multidimensional data on wearable display devices, for example, a head mounted display device.

Exemplary embodiments of apparatus and methods that facilitate displaying imaging data in ultrasound imaging systems are described above in detail. A technical effect of reducing the dimensionality of ultrasound image data from a first dimensional representation to a reduced dimensional representation, searching the reduced dimension data for a feature of interest and displaying the feature of interest in the first dimensional representation as described herein include at least one of facilitating visualizing regions of interest in a scanned object.

It will be recognized that although the system in the disclosed embodiments comprises programmed hardware, for example, software executed by a computer or processor-based control system, it may take other forms, including hardwired hardware configurations, hardware manufactured in integrated circuit form, firmware, among others. It should be understood that the intensity projection map processor disclosed may be embodied in a hardware device or may be embodied in a software program executing on a dedicated or shared processor within the ultrasound system or may be coupled to the ultrasound system.

The above-described methods and apparatus provide a cost-effective and reliable means for facilitating the viewing multi-dimensional image data by reducing the dimensionality of the image data to reduce the computing power needed to scout the data to select a view. More specifically, the methods and apparatus facilitate improving visualization of multi-dimensional data. As a result, the methods and apparatus described herein facilitate operating multi-dimensional ultrasound systems in a cost-effective and reliable manner.

Exemplary embodiments of ultrasound imaging systems are described above in detail. However, the systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for operating an ultrasound imaging system, said method comprising:
   receiving an image data set of a region of interest in a first dimensional representation that comprises at least three dimensions;
   receiving a selected view perspective of the image data set determined by a viewpoint selector;
   generating, with a processor, a plurality of planar slices of image data of the image data set, an axis of the planar slices being orthogonal to the selected view perspective;
   reducing the dimensionality of the image data set to a second dimensional representation;
   receiving a selected feature of interest selected in the second dimensional representation;
   generating an image corresponding to the selected feature of interest; and
   displaying the image corresponding to the selected feature in the first dimensional representation on a display system.

2. A method in accordance with claim 1 further comprising generating with the processor a difference map of respective pixels of each adjacent pair of planar slices.

3. A method in accordance with claim 1 wherein the first-dimensional representation comprises four dimensions and further comprising generating with the processor a plurality of volume datasets of image data of the four-dimensional data set relative to the selected view perspective.

4. A method in accordance with claim 3 further comprising generating with the processor a difference map of respective pixels of each temporally adjacent pair of volume datasets.

5. A method in accordance with claim 1 wherein reducing the dimensionality of the image data set comprises generating with the processor a difference map of respective pixels of each adjacent pair of planar slices using at least one of an intensity projection map, a sum of absolute differences, a maximum intensity projection map, a minimum intensity projection map, an average intensity projection map, an integrated projection map, a first local maximum projection map, and an arbitrarily weighted projection map.

6. A method in accordance with claim 1 further comprising outputting a display of the first dimensional representation and the second dimensional representation concurrently on the display system.

7. A method in accordance with claim 1 further comprising outputting a display of a second dimensional representation index indicator on the display system.

8. A method in accordance with claim 1 wherein selecting a feature of interest in the second dimensional representation comprises:
   outputting a display of a second dimensional representation index indicator; and
   manipulating an index selector with a user input to align the index indicator with a portion of the feature of interest.

9. A method in accordance with claim 1 further comprising displaying the second dimensional representation of the image data set.

10. A method in accordance with claim 1 further comprising generating an image corresponding to the selected feature of interest.

11. A method in accordance with claim 1 wherein displaying an image corresponding to the selected feature in the first dimensional representation on a display system is based on the image data in at least one of the first dimensionality and the second dimensionality.

12. An ultrasound system comprising:
   an ultrasound probe having at least one transducer for transmitting pulses to an object;
   a processor programmed to receive image data in a first dimensionality and reduce the image data to a second dimensionality;
   a viewpoint selector coupled to a user input of said ultrasound system to control a view of reduced image data; and
   a display system comprising an ultrasound viewing area and a reduced dimensionality display area, wherein said processor is configured to display in the ultrasound viewing area, ultrasound images based on the image data in at least one of the first dimensionality and the second dimensionality as determined by a position of the viewpoint selector in the reduced image data view, and difference maps based on the image data in the first dimensionality.

13. An ultrasound system in accordance with claim 12 further comprising a view perspective selector for orienting the received image data based on a selected image axis.

14. An ultrasound system in accordance with claim 13 wherein said view perspective selector is configured to at least one of flip and rotate said received image data about said selected image axis.

15. An ultrasound system in accordance with claim 13 wherein said view perspective selector comprises a pointing device.

16. An ultrasound system in accordance with claim 13 wherein said processor is further configured to receive a user view command from said view perspective selector.

17. An ultrasound system in accordance with claim 12 wherein said processor is configured to reduce the image data to the second dimensionality using at least one of an intensity projection map, a sum of absolute differences, a maximum intensity projection map, a minimum intensity projection map, an average intensity projection map, an integrated projection map, a first local maximum projection map, and an arbitrarily weighted projection map.

18. An ultrasound system in accordance with claim 12 wherein said reduced dimensionality display area is configured to display an indication of difference between adjacent pairs of image slices of the received image data.

19. An ultrasound system in accordance with claim 12 wherein said reduced dimensionality display area is configured to display an indication of difference between temporally adjacent pairs of image volumes of the received image data.

20. An ultrasound system in accordance with claim 12 wherein said display system comprises an image display that is wearable by a user.

21. An ultrasound system in accordance with claim 12 wherein said processor is programmed to receive image data over a period of time.

22. An ultrasound system in accordance with claim 12 wherein said difference maps of received image data over a period of time comprise a linear map of the received image data indicative of an amount of image change between images over the period of time, and wherein the reduced dimensionality display area is configured to display said linear map.

23. An ultrasound system in accordance with claim 12 wherein said display system is configured to display data within the ultrasound viewing area and the reduced dimensionality display area concurrently.

24. A method for processing ultrasound data, said method comprising:
   receiving multidimensional ultrasound data comprising N dimensions, wherein the value of N is one of three and four;
   generating, with a processor, a reduced dimension data set from the multidimensional ultrasound data with the processor, the reduced dimension data set comprising N−1 dimensions;
   receiving a selected feature of interest in the reduced dimension data set based on a user input;
   generating an image corresponding to the selected feature of interest; and
   displaying the image comprising the N dimensions that corresponds to the feature of interest on a display system.

25. A method in accordance with claim 24 wherein generating a reduced dimension data set from the multidimensional ultrasound data comprises creating a difference map from the received multidimensional ultrasound data.

26. A method in accordance with claim 24 further comprising configuring the data for display as a holographic image on the display system.

27. A method in accordance with claim 24 wherein the receiving comprises receiving the multidimensional ultrasound data only from a selected region of interest.

28. A method in accordance with claim 24 wherein generating a reduced dimension data set from the multidimensional ultrasound data comprises using an intensity projection map, a sum of absolute differences, a maximum intensity projection map, a minimum intensity projection map, an average intensity projection map, an integrated projection map, a first local maximum projection map, and an arbitrarily weighted projection map to generate the reduced dimension data set.

29. A method in accordance with claim 28 wherein generating a reduced dimension data set from the multidimensional ultrasound data comprises generating a reduced dimension data set that is configured for user navigation.

30. A method in accordance with claim 29 wherein generating a reduced dimension data set that is configured for user navigation comprises generating a reduced dimension data set that is configured for angle planar reformatting to provide different views.

31. A method in accordance with claim 30 wherein generating a reduced dimension data set that is configured for angle planar reformatting to provide different views comprises reformatting the reduced dimension data set dynamically.

32. An ultrasound system in accordance with claim 12 wherein the first-dimensionality comprises three-dimensions and the second dimensionality comprises two-dimensions, and the reduced dimensionality display area includes a scout map area displaying the difference maps with at least one of a scale and an index indicator.

33. An ultrasound system in accordance with claim 12 wherein the processor is configured to calculate a total difference between each pair of image slices corresponding to the difference maps.

34. An ultrasound system in accordance with claim 12 wherein the processor is configured to calculate and normalize a total difference between each pair of image slices corresponding to the difference maps.

35. An ultrasound system in accordance with claim 12 wherein the processor is configured to identify image data tagged via the user input and wherein the display provides an identification of the tagged image data on the ultrasound images.

36. An ultrasound system in accordance with claim 12 wherein the processor is configured to identify a multi-dimensional structure in the image data based on matching features to a structural model and wherein the display provides an identification of the multi-dimensional structure on the ultrasound images.

* * * * *